(12) United States Patent
Bagneris

(10) Patent No.: US 11,953,693 B2
(45) Date of Patent: Apr. 9, 2024

(54) ATHLETIC EYEGLASSES SYSTEM AND METHOD

(71) Applicant: Cedric Bagneris, New Orleans, LA (US)

(72) Inventor: Cedric Bagneris, New Orleans, LA (US)

( * ) Notice: Subject to any disclaimer, the term of this patent is extended or adjusted under 35 U.S.C. 154(b) by 0 days.

(21) Appl. No.: 17/157,406

(22) Filed: Jan. 25, 2021

(65) Prior Publication Data
US 2022/0236577 A1 Jul. 28, 2022

(51) Int. Cl.
| | |
|---|---|
| *G02B 27/01* | (2006.01) |
| *A63B 71/06* | (2006.01) |
| *G02C 5/14* | (2006.01) |
| *G02C 11/00* | (2006.01) |
| *G06F 3/02* | (2006.01) |
| *G06F 3/14* | (2006.01) |

(52) U.S. Cl.
CPC ...... *G02B 27/0176* (2013.01); *A63B 71/0622* (2013.01); *A63B 71/0686* (2013.01); *G02B 27/0172* (2013.01); *G02C 5/14* (2013.01); *G02C 11/10* (2013.01); *G06F 3/0202* (2013.01); *G06F 3/1423* (2013.01); *A63B 2071/065* (2013.01); *A63B 2071/0666* (2013.01); *A63B 2071/0675* (2013.01); *A63B 2071/0694* (2013.01); *A63B 2220/40* (2013.01); *A63B 2220/808* (2013.01); *A63B 2220/836* (2013.01); *A63B 2230/06* (2013.01); *A63B 2230/207* (2013.01); *G02B 2027/0141* (2013.01); *G02B 2027/0178* (2013.01)

(58) Field of Classification Search
CPC ............ G02B 27/0176; G02B 27/0172; G02B 2027/0141; G02B 2027/0178; A63B 71/0622; A63B 71/0686; A63B 2071/065; A63B 2071/0666; A63B 2071/0675; A63B 2071/0694; A63B 2220/40; A63B 2220/808; A63B 2220/836; A63B 2230/06; A63B 2230/207; G02C 5/14; G02C 11/10; G06F 3/0202; G06F 3/1423
See application file for complete search history.

(56) References Cited

U.S. PATENT DOCUMENTS

| | | | |
|---|---|---|---|
| 4,753,514 | A | 6/1988 | Kubik |
| 7,972,245 | B2 | 7/2011 | Temple et al. |
| 8,177,361 | B2 | 5/2012 | Sessner et al. |
| 9,579,060 | B1 | 2/2017 | Lisy et al. |
| 9,870,716 | B1 | 1/2018 | Rao et al. |
| 10,085,675 | B2 * | 10/2018 | Nagasaki ............. A61B 5/7282 |

(Continued)

FOREIGN PATENT DOCUMENTS

JP 6332830 B2 5/2018

*Primary Examiner* — Sahlu Okebato
(74) *Attorney, Agent, or Firm* — KEATY LAW FIRM LLC

(57) ABSTRACT

An athletic eyeglasses system and method for monitoring and displaying to an athlete relevant information such as elapsed time and heart rate, in real time, without diversion of attention from the view ahead and without extraneous movement of hands or arms, providing an eyeglasses frame, two frame arms, two display glass units having data displays, a controller unit, a battery, a covered port for charging the battery, input buttons, a timer starter, and a sensor to sense physiological conditions such as heart rate and peripheral oxygen saturation.

20 Claims, 3 Drawing Sheets

(56) References Cited

U.S. PATENT DOCUMENTS

| | | | |
|---|---|---|---|
| 10,497,470 B2 | 12/2019 | Chi et al. | |
| 10,789,480 B2* | 9/2020 | Martin | G06F 16/5854 |
| 2011/0221746 A1* | 9/2011 | Park | G02B 30/24 |
| | | | 359/464 |
| 2013/0342805 A1* | 12/2013 | Huang | G02C 9/02 |
| | | | 351/158 |
| 2015/0168723 A1* | 6/2015 | Eto | H04N 13/344 |
| | | | 348/51 |
| 2017/0255262 A1* | 9/2017 | Liu | G06F 3/015 |

* cited by examiner

ATHLETIC EYEGLASSES SYSTEM AND METHOD

BACKGROUND OF THE INVENTION

This invention provides an athletic eyeglasses system and method for monitoring and displaying to an athlete relevant information such as elapsed time and heart rate, in real time.

In many athletic activities the element of time is very important, and it is desirable and useful to see the elapsed time during performance of the activity. Looking at a timekeeping device such as a wristwatch or stopwatch, however, requires at least momentarily diverting attention and focus away from the athletes view of what is ahead. In some activities even momentary diversion of attention can be dangerous or otherwise disadvantageous. And intermittent glances at a watch only provide intermittent information about time. In some activities, the disposition of the arms and hands is limited by considerations of balance or of propulsion, making any device held in the hand or mounted on the wrist or arm even less useful.

Also important in many athletic activities, such as distance or endurance running, riding, or rowing, it is beneficial to be able to monitor, in real time, the measure of one or more physiological conditions, such as heart rate or pulse rate, in order to make better-informed expenditures of energy. Again, the necessity of at least momentarily diverting attention and focus to look at a device can be dangerous or disadvantageous, and only provides intermittent information.

What is needed is a system and method for determining and displaying the relevant information about time and physiological condition, in real time, in a way that can be seen and comprehended by the athlete without any diversion of attention or focus and without any extraneous movement of the hands or arms.

U.S. Pat. No. 7,972,245 for "Presenting Information to Users During an Activity, Such As Information from a Previous or Concurrent Outdoor, Physical Activity," issued on Jul. 5, 2011 to assignee T-Mobile USA, Inc., provides for a system and method for providing information during an activity. In some examples, the system includes a capture device that captures information during a first activity and a presentation device that presents the information during a second activity. In some examples, the system employs and is implemented on one or more mobile devices that transfer, process, and generate information based on performance of activities.

U.S. Pat. No. 9,579,060 for a "Head-Mounted Physiological Signal Monitoring System, Devices and Methods," issued on Feb. 28, 2017 to assignee Orbitol Research Inc., provides for a hat, helmet, and other headgear apparatus including dry electrophysiological electrodes and, optionally, other physiological and/or environmental sensors to measure signals such as ECG from the head of a subject. Methods of use of such apparatus to provide fitness, health, or other measured or derived, estimated, or predicted metrics are also disclosed.

Japanese Patent No. 6332830 for an "Exercise Support System, Exercise Support Method, and Exercise Support Program," issued on May 30, 2018 to assignee Casio Computer Co., Ltd., provides for an exercise support system comprising a wrist device and a chest device for acquiring sensor data or the like during a running motion; an imaging device for acquiring a running image by synchronizing with the sensor data or the like; a network server for processing and analyzing the sensor data or the like and the running image, and generating advice data that includes a comparison image consisting of one-cycle running images of a user and an elite runner, an indicator displayed while being superimposed on the comparison image for each instruction item, and an advice text corresponding to the instruction items; and a user terminal or the like for displaying the advice data through the network in a predetermined display mode.

US Patent Application Publication No. 2017/0255262 for "Smart Sports Eyewear," published on Sep. 7, 2017 by assignee Xiaoyi Technology Co., Ltd., discloses a wearable device. According to certain embodiments, the wearable device may include a display component configured to display a virtual image. The wearable device may also include a first sensor configured to generate a first signal indicative of a physiological condition of a user. The wearable device may further include a controller configured to: determine the physiological condition based on the first signal; and control the display component to display the physiological condition.

U.S. Pat. No. 10,497,470 for a "Mobile Terminal and Controlling Method Thereof," issued on Dec. 3, 2019 to assignee LG ELECTRONICS INC., provides for a mobile terminal including a memory configured to store at least one of first information on a disease history of a preset user and second information on a preset disease; a wireless communication unit configured to receive information obtained through a sensor of a preset external device, wherein the received information comprises at least one of third information obtained from sensing a surrounding environment of the preset external device and fourth information obtained from sensing a current state of the preset user; a display unit; and a controller configured to determine a current health-related state of the preset user using at least one of the first information, the second information and the received information, determine a cause of the current health-related state of the preset user using at least one of the first information, the second information and the received information, and output information about the determined cause of the current health-related state of the preset user.

U.S. Pat. No. 4,753,514 for a "Headwear-Mounted Periscopic Display Device," issued on Jun. 28, 1988 to assignee Iota Instrumentation Co., provides for a periscopic display device for close up viewing of a display. The device includes means for generating a display, such as an LED, LCD, or ELD display, and periscopic means consisting of a body of optically clear material having a reflecting prism portion and a collimating lens portion. The prism portion includes a first planar surface positioned parallel and adjacent to the display and a plurality of optically aligned reflecting surfaces for transmitting a reflected image of the display. The collimating lens portion consists of a convex lens having a focal point at the display and is positioned to receive the reflected image for focusing the image at optical infinity. Preferably the body includes a mounting portion in which the display generating means is embedded. The display device is lightweight, waterproof, dustproof, and is easily mounted on the eyeglass frames, visor, or headband of the wearer.

U.S. Pat. No. 9,870,716 for "Smart Glasses and Smart Watches for Real Time Connectivity and Health," issued on Jan. 16, 2018 to inventors Sanjay K. Rao et al., provides for a system for wearable devices including intelligent electronic devices, smart glasses, smart watches, and smart devices. A variety of sensors may be integrated into a wearable smart watch device for health management, voice commands, and lifestyle management. The glasses may continuously screen the food consumed by an individual and analyze the food content based on the size of the morsel, consistency, transparency, and other factors. This may further enable an individual to keep track of daily calorie intake and nutritional value will help in healthy diet and glasses will help in maintaining a healthy weight management. The device may image various people and assess health factors including hydration rate, skin health such as skin rashes, and pulse rates. This may be determined using image recognition and shining a light source on the skin to determine the rate of blood flow and refractory of the light.

U.S. Pat. No. 8,177,361 for a "Spectacle Glass and Spectacle Lens for Data Reflection," issued on May 15, 2012 to assignee Rodenstock GmbH, provides for a spectacle lens having a first and a second surface, wherein at least the first surface of the spectacle lens has a major portion zone and at least one prism zone. The major portion zone of the first surface, together with the opposing second surface of the spectacle lens, forms a major portion of the spectacle lens, which is designed for vision in at least a predetermined distance. The prism zone of the first surface, together with the opposing second surface of the spectacle lens, forms a prism portion, which is designed and arranged such that an optical image of a display is formed at a predetermined virtual distance in front of the eyes of the spectacle wearer. The invention further relates to spectacles, which comprise the spectacle lens, and to a method and apparatuses for calculating or optimizing and producing the spectacle lens.

SUMMARY OF THE INVENTION

This invention provides an athletic eyeglasses system and method for monitoring and displaying to an athlete relevant information such as elapsed time and heart rate, in real time.

The athletic eyeglasses system provides an eyeglasses frame, two frame arms, two display glass units having data displays, a controller unit, a battery, a covered port for charging the battery, input buttons, a timer starter, and a sensor to sense physiological conditions such as heart rate and peripheral oxygen saturation.

BRIEF DESCRIPTION OF THE DRAWINGS

Reference will now be made to the drawings, wherein like parts are designated by like numerals, and wherein.

DETAILED DESCRIPTION OF THE INVENTION

Figure 1:
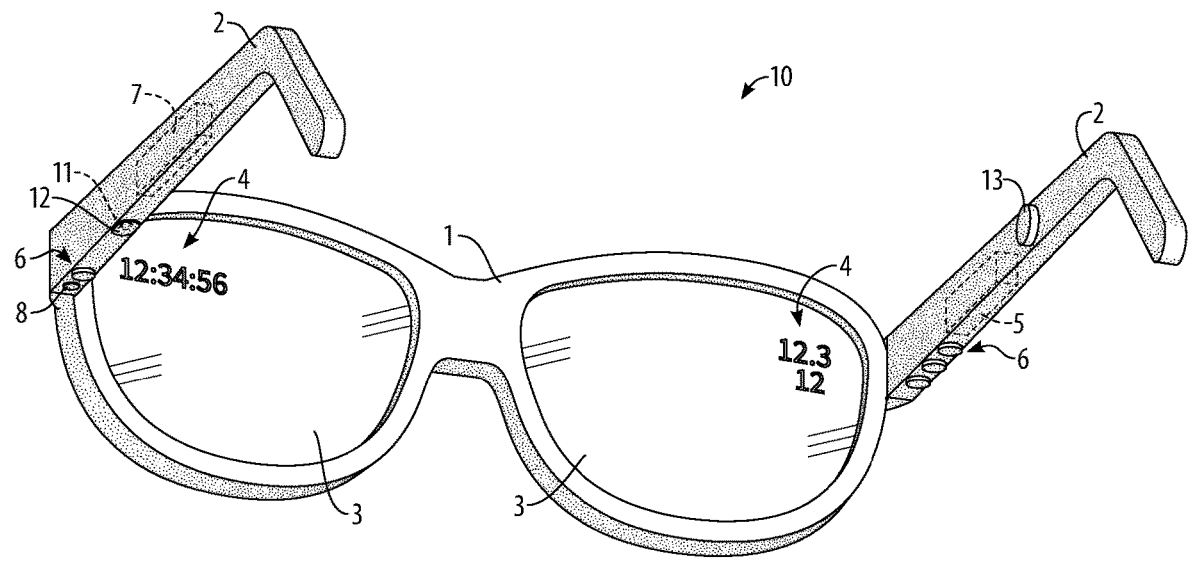
FIG. 1 is a perspective view of an embodiment of the athletic eyeglasses system of the invention.

Referring to FIG. 1, the athletic eyeglasses system 10 and method monitors and reports data regarding time and physiological condition to an athlete such as a runner, in real time, in a way which does not require looking away from the normal view forward ahead of the athlete. For a running athlete, the relevant time data is likely to be the time elapsed since a starting signal such as a starter's gun, and the relevant physiological data is likely to be heart rate or pulse rate. The availability of this data in real time and without diverting attention from the conditions ahead can be beneficial to an athlete, especially during an event requiring controlled use of physical resources, such as distance or endurance running, riding, or rowing.

An eyeglasses frame 1 and two frame arms 2 are provided, as shown, and form a glasses frame for the athlete to wear in the usual way. Two display glass units 3 are mounted in the eyeglasses frame 1. Each display glass unit 3 provides one or more data displays 4, as shown, which display data within the athlete's field of vision such that the athlete does not need to look away from what would normally be looked at during his or her athletic activity. The data displays 4 can be implemented using technology known in the art, such as liquid crystal display technology.

Power for the data displays 4 and other functioning of the athletic eyeglasses 10 is provided by a battery 5 mounted within one of the frame arms 2. One or more input buttons 6 are provided on one or both frame arms 2. The input buttons 6 can be used, for example, for activation and deactivation of the system, for adjusting the intensity or size of the data displays 4, for switching between modes such as a day mode and night mode, or for adjusting exactly what data is displayed and exactly how it is displayed.

A controller unit 7 mounted within one of the frame arms 2 is provided, which controls the display of data by the data displays 4, including the obtaining of data from sensors 13, 14, as disclosed below, and the keeping of time to be displayed.

A timer starter 8 is provided to trigger the measurement and display of elapsed time through the controller unit 7. The timer starter 8 can be implemented as a button, which might be appropriate in some circumstances such as self-directed training. Reaching to press a button at the start of an athletic event is likely not an advantageous nor accurate way to start the timer in most circumstances. In an embodiment of the athletic eyeglasses 10, the timer starter 8 can be implemented as a sound-activated trigger which reacts to a loud sharp noise such as a starter's gun, or a horn, or a buzzer. In another embodiment of the athletic eyeglasses 10, the timer starter 8 can be implemented as an accelerometer which reacts to the initial acceleration at the start of an event. Yet another embodiment can provide multiple implementations of the timer starter 8 function, with a provision for choosing among the implementations.

A port 11 having a port cover 12 is provided on one of the frame arms 2. The port 11 provides for charging the battery 7 by accepting the power to do so. The controller unit 7 can control the charging process to prevent overcharging. In an embodiment of the athletic eyeglasses 10, the port 11 can also be used for transfer of data into and out of the controller unit 7. The port 11 can be a USB port operating under the applicable USB standards.

A sensor 13 mounted to a frame arm 2 is provided for the purpose of sensing one or more physiological measurements, such as heart rate or pulse rate. A sensor measuring pressure, sound, temperature, electrical properties, or other indicators might be used. More than one sensor can be provided and might be necessary when measuring some types of physiological conditions. The sensor 13 or sensors can be placed along one or both frame arms 2 in order to best sense the physiological condition. A measurement of heart rate or pulse rate is likely to be an important measurement for display for most uses of the athletic eyeglasses 10.

Figure 2:
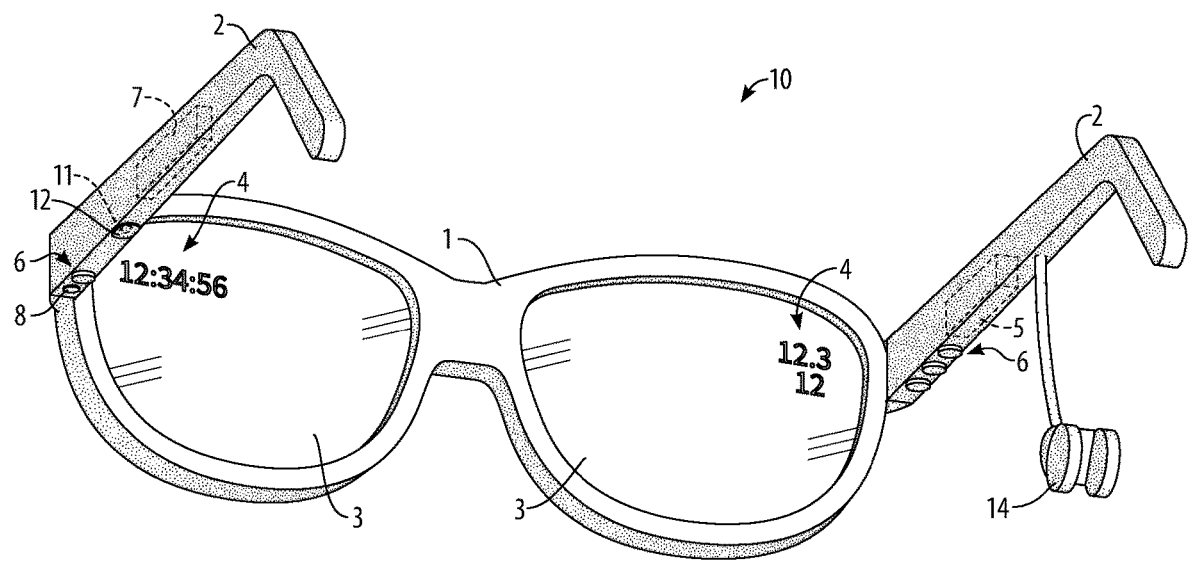
FIG. 2 is a perspective view of another embodiment of the athletic eyeglasses system of the invention having a tethered sensor.

Referring to FIG. 2, in an embodiment of the athletic eyeglasses 10 the sensor, or one of the sensors, can be a tethered sensor 14, as shown.

Peripheral oxygen saturation (SpO2) is an estimate of the percentage of oxygenated hemoglobin in the blood. Peripheral oxygen saturation is measured by pulse oximetry, where a device shines light through a peripheral part of the body, usually a finger or an earlobe, and measures the absorption of light. Real-time availability of SpO2 data can be beneficial to an athlete, especially in distance or endurance events. Determining peripheral oxygen saturation (SpO2) might best be done using a tethered sensor 14 which clips to the earlobe. Heart rate or pulse rate can also be determined when using pulse oximetry, and both the peripheral oxygen saturation and the pulse rate might be displayed on the data display 4 of the athletic eyeglasses 10.

Figure 3:
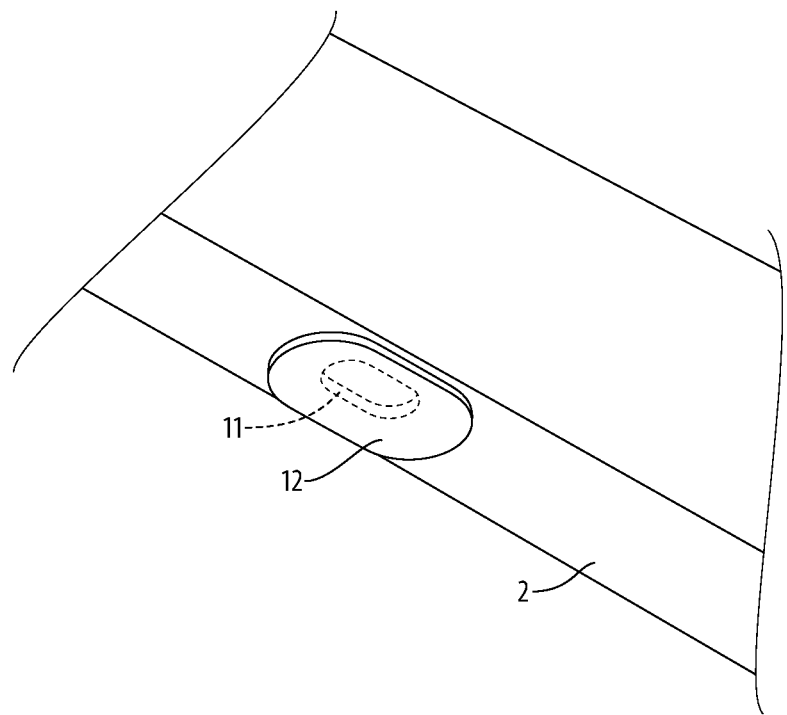
FIG. 3 is a detail view of the port and port cover of the athletic eyeglasses system with the port cover closed.
Figure 4:
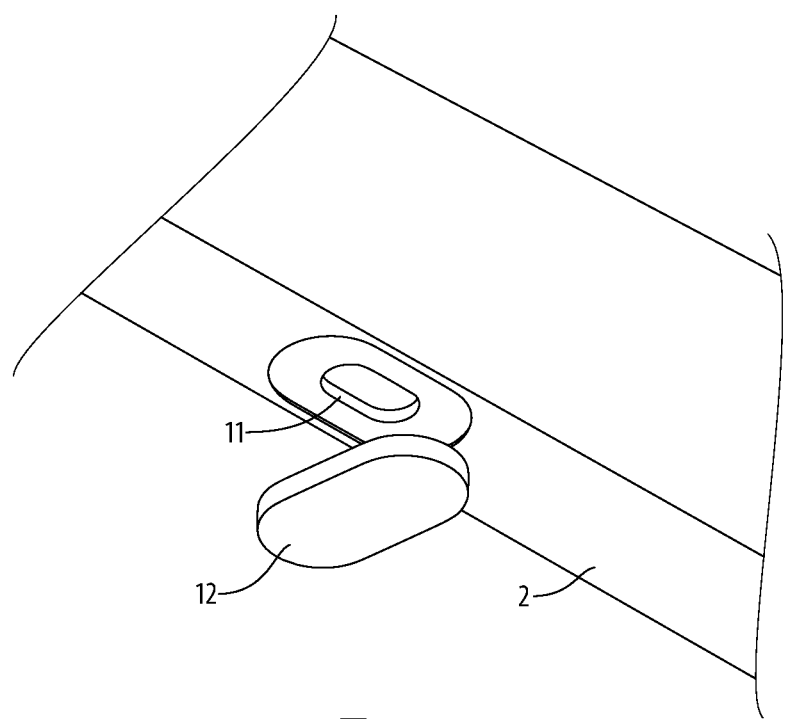
FIG. 4 is a detail view of the port and port cover of the athletic eyeglasses system with the port cover opened.

Referring to FIG. 3 and FIG. 4, the port 11 located on a frame arm 2, which is used for charging the battery 5 and optionally used for input and output of data to and from the controller unit 7, is covered by a port cover 12, for protection against intrusion of water, dust, or sweat during use or during storage. The port cover 12 can be moved out of the way for charging or data transfer.

Figure 5:
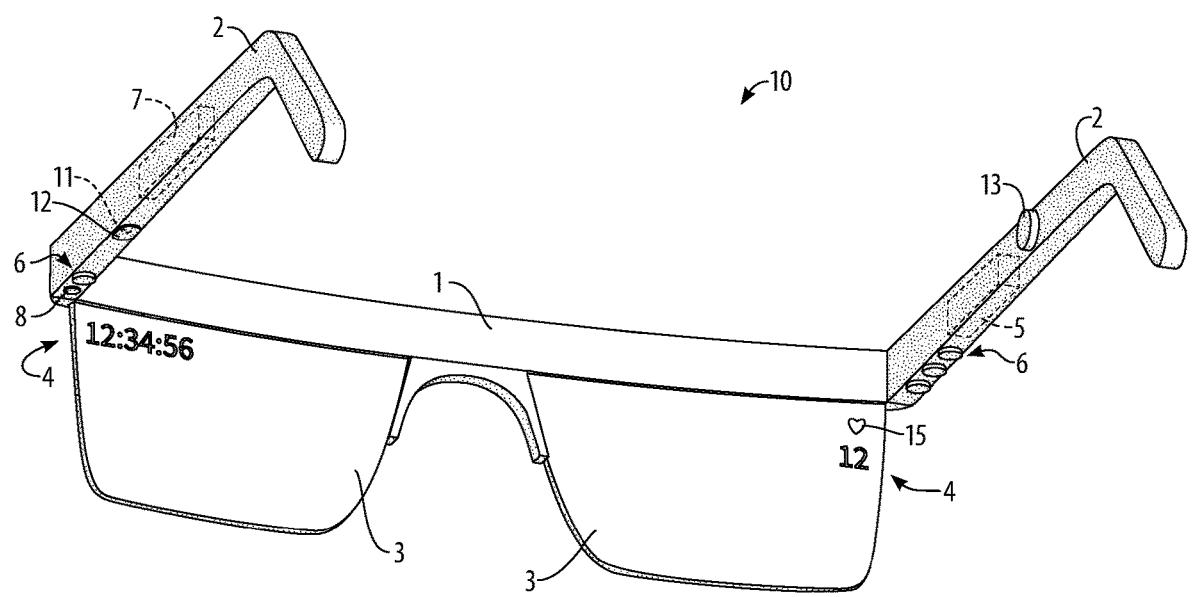
FIG. 5 is a perspective view of another embodiment of the athletic eyeglasses system of the invention having symbols on the data displays.

Referring to FIG. 5, in another embodiment of the athletic eyeglasses 10, the eyeglasses frame 1 has a different configuration but the same function. The data displays 4 can show symbols such as numerals, alphabetic characters, and graphic symbols, such as the heart symbol 15 shown, which can be made to flash or pulse in a rhythm tracking the heart rate, or can be made to appear, flash, or change color when a defined value of data is detected.

Many other changes and modifications can be made in the system and method of the present invention without departing from the spirit thereof. I therefore pray that my rights to the present invention be limited only by the scope of the appended claims.

I claim:

1. An athletic eyeglasses system comprising:
   (i) an eyeglasses frame;
   (ii) two frame arms mounted upon said eyeglasses frame;
   (iii) two display glass units mounted into said eyeglasses frame;
   (iv) at least two data displays incorporated into said display glass units, each adapted to display time, or physiological-condition data, or both;
   (v) a controller unit mounted within one said frame arm, adapted to control the display of data through said data displays;
   (vi) a battery mounted within one said frame arm, adapted to provide stored power for operation of said controller unit and said data displays;
   (vii) at least one input button mounted upon at least one said frame arm, adapted to facilitate user control of said controller unit;
   (viii) a timer starter mounted upon one said frame arm, adapted to sense a start of a triggering event in response to a signal received from an exterior source and to initiate keeping of time and, separately, elapsed time from the start of the triggering event for display through said data displays, said controller unit being adapted to control display of data generated by the timer in numerical form while the eyeglasses system is being worn by a user during an athletic activity;
   (ix) a port mounted upon one said frame arm, adapted to accept power to charge said battery;
   (x) a port cover adapted to seal said port during athletic use; and
   (xi) at least one sensor mounted upon at least one said frame arm, adapted to sense at least one physiological condition for display through said data displays.

2. The athletic eyeglasses system of claim 1, where said sensor further comprises a tethered sensor connected to a frame arm by a tethering line.

3. The athletic eyeglasses system of claim 1, where said sensor is further adapted to sense the physiological condition of heart rate.

4. The athletic eyeglasses system of claim 1, where said sensor is further adapted to sense the physiological condition of peripheral oxygen saturation.

5. The athletic eyeglasses system of claim 1, where said sensor is further adapted to sense the physiological conditions of heart rate and peripheral oxygen saturation.

6. The athletic eyeglasses system of claim 1, where said timer starter is further adapted to sense the start of the triggering event by sensing a sound signal generated by an exterior source.

7. The athletic eyeglasses system of claim 1, where said timer starter is further adapted to sense the start of the triggering event by sensing a change of acceleration.

8. The athletic eyeglasses system of claim 1, where said port is further adapted to facilitate input and output of data to and from said controller unit.

9. The athletic eyeglasses system of claim 1, where said port is a USB port.

10. The athletic eyeglasses system of claim 1, where said data display is further adapted to display time and physiological-condition data through numeric, alphabetical, and graphic symbols.

11. An athletic eyeglasses method comprising:
    (i) providing an athletic eyeglasses system comprising:
       (a) an eyeglasses frame;
       (b) two frame arms mounted upon said eyeglasses frame;
       (c) two display glass units mounted into said eyeglasses frame;
       (d) at least two data displays incorporated into said display glass units, each adapted to display time, or physiological-condition data, or both;
       (e) a controller unit mounted within one said frame arm, adapted to control the display of data through said data displays;
       (f) a battery mounted within one said frame arm, adapted to provide stored power for operation of said controller unit and said data displays;
       (g) at least one input button mounted upon at least one said frame arm, adapted to facilitate user control of said controller unit;
       (h) a timer starter mounted upon one said frame arm, adapted to sense a start of a triggering event in response to a signal received from an exterior source and to initiate keeping of time and, separately, elapsed time from the start of the triggering event for display through said data displays, said controller unit being adapted to control display of data generated by the timer in numerical form while the eyeglasses system is being worn by a user during an athletic activity;
       (i) a port mounted upon one said frame arm, adapted to accept power to charge said battery;
       (j) a port cover adapted to seal said port during athletic use; and
       (k) at least one sensor mounted upon at least one said frame arm, adapted to sense at least one physiological condition for display through said data displays;

(ii) wearing said athletic eyeglasses system in the manner of eyeglasses; and
(iii) seeing the time and physiological-condition data in real-time during athletic activity without diversion of attention from the view ahead and without extraneous movement of hands or arms.

12. The athletic eyeglasses method of claim 11, where said sensor of the athletic eyeglasses system further comprises a tethered sensor connected to a frame arm by a tethering line.

13. The athletic eyeglasses method of claim 11, where said sensor of the athletic eyeglasses system is further adapted to sense the physiological condition of heart rate.

14. The athletic eyeglasses method of claim 11, where said sensor of the athletic eyeglasses system is further adapted to sense the physiological condition of peripheral oxygen saturation.

15. The athletic eyeglasses method of claim 11, where said sensor of the athletic eyeglasses system is further adapted to sense the physiological conditions of heart rate and peripheral oxygen saturation.

16. The athletic eyeglasses method of claim 11, where said timer starter of the athletic eyeglasses system is further adapted to sense the start of the triggering event by sensing a sound signal generated by an exterior source.

17. The athletic eyeglasses method of claim 11, where said timer starter of the athletic eyeglasses system is further adapted to sense the start of the triggering event by sensing a change of acceleration.

18. The athletic eyeglasses method of claim 11, where said port of the athletic eyeglasses system is further adapted to facilitate input and output of data to and from said controller unit.

19. The athletic eyeglasses method of claim 11, where said port of the athletic eyeglasses system is a USB port.

20. The athletic eyeglasses method of claim 11, where said data display is further adapted to display time and physiological condition data through numeric, alphabetical, and graphic symbols.

* * * * *